United States Patent
Guhl et al.

(12)

(10) Patent No.: US 6,197,186 B1
(45) Date of Patent: Mar. 6, 2001

(54) PROCESS FOR PREPARING SILVER COMPOUNDS

(75) Inventors: Dieter Guhl, Speyer; Frank Houselmann, Weingarten, both of (DE)

(73) Assignee: Th. Goldschmidt Ag, Essen (DE)

( * ) Notice: Subject to any disclaimer, the term of this patent is extended or adjusted under 35 U.S.C. 154(b) by 0 days.

(21) Appl. No.: 09/165,548

(22) Filed: Oct. 2, 1998

(30) Foreign Application Priority Data

Feb. 10, 1997 (DE) .............................. 197 43 613

(51) Int. Cl.$^7$ .............................. C25B 3/12; C25B 3/00; C25B 3/06
(52) U.S. Cl. .......................... 205/457; 205/445; 205/455; 205/459
(58) Field of Search ................................. 205/445, 455, 205/457, 459

(56) References Cited

U.S. PATENT DOCUMENTS

| 5,491,247 | 2/1996 | Gernon ................................. 556/113 |
| 5,618,404 | 4/1997 | Okuhama et al. .................... 205/445 |

FOREIGN PATENT DOCUMENTS

| 85/03530 | * | 8/1985 | (WO) . |
| WO 85/03530 | | 8/1985 | (WO) . |

OTHER PUBLICATIONS

Japanese Patent Application No. 05,213,854 (abstract) ; Aug. 24, 1993.

\* cited by examiner

*Primary Examiner*—Edna Wong
(74) *Attorney, Agent, or Firm*—Scully, Scott, Murphy & Presser

(57) ABSTRACT

The invention relates to a process for preparing silver compounds. The process relates to the preparation of silver compounds of the general formula (I)

$$RSO_3Ag \qquad (I)$$

where

R is an unsubstituted or substituted, linear or branched, saturated, monounsaturated or polyunsaturated alkyl or alkenyl radical having 1 to 9 carbon atoms or an unsubstituted or substituted aryl radical having 6 to 12 carbon atoms, which comprises subjecting acid of the general formula (II)

$$RSO_3H \qquad (II)$$

where

R has the above mentioned meaning, to an electrolytic dissolution of the anode in a membraneless electrolysis cell having metallic silver as anode.

8 Claims, No Drawings

PROCESS FOR PREPARING SILVER COMPOUNDS

FIELD OF THE INVENTION

The invention relates to a membraneless process for preparing silver compounds.

BACKGROUND OF THE INVENTION

Electrolytes for chemical silvering comprising silver nitrate and thiourea or similar compounds are used as electrolytes for metal deposition. In the case of silver electrolytes especially, however, alternatives to silver nitrate or silver cyanide are wanted.

Electrolytes for chemical silvering comprising silver nitrate and thiourea or similar compounds have a tendency to explosive decomposition on drying.

Virtually only alkaline cyanide-containing electrolytes comprising silver cyanide are used for electrodeposition. These electrolytes have the disadvantage of their high toxicity. In addition, masking lacquers of electronic components are attacked by these electrolytes. Furthermore, these electrolytes permit only relatively low current densities/deposition rates. Nitric acid electrolytes comprising silver nitrate are unsuitable for the electrodeposition of metals, since the nitrate is destroyed by cathodic reduction.

Other silver salts obtainable on an industrial scale, such as silver chloride or silver sulfate, are unsuitable for preparing chloride or sulfated electrolytes, since the water solubility of these silver compounds is too low.

In contrast thereto, the high water solubility of silver methane sulfonate is known, so that this compound and specific silver alkylsulfonates or arylsulfonates are of interest as an alternative to the known electrolytes as an electrolyte for the electrodeposition of silver.

WO 85/03530 describes a process for preparing heavy metal carboxylates. Page 6, line 14 also mentions silver as one of the heavy metals. Page 14, line 27 to page 15, line 5 further describes the fact that sulfonic acid salts, e.g. of p-toluenesulfonic acid, can also be prepared by this process. However, none of the exemplary embodiments indicates the use of silver.

In the paragraph extending over pages 3 and 4, it is stated that the electrolyte shall comprise an ionic component which readily dissociates into anions and cations, in particular alkali metal halides, in particular sodium chloride, being proposed.

As is known, silver halides are sparingly soluble in aqueous solutions, so that in the event of anodic dissolution of silver in a sodium-chloride-containing electrolyte, silver chloride would immediately precipitate.

U.S. Pat. No. 5,618,404 describes an electrolytic process for preparing lead and tin sulfonates which, however, includes a complex separation of the anodic region from the cathodic region by cation and anion exchange membranes.

JP 0 521 38 54 A2 (CA 119:270800) discloses a process for preparing silver sulfonate salts. A solution of silver carbonate in methyl cyanide is reacted with a solution of methanesulfonic acid in methyl cyanide, in order to obtain 93% pure silver methylsulfonate. Furthermore, it is also known to prepare silver methanesulfonate from aqueous methanesulfonic acid and silver carbonate or silver oxide, or from aqueous methanesulfonic acid, silver powder and, if appropriate, hydrogen peroxide (U.S. Pat. No. 5,491,247 A). However, the above mentioned processes are very costly, since the silver is generally initially dissolved in nitric acid in order to prepare the silver carbonate or silver oxide and then to react this compound with methanesulfonic acid. Although the preparation from the metal using hydrogen peroxide is cheaper, a large metal surface area is necessary for acceptable reaction times. This determines the necessity of using expensive metal powder. Furthermore, there is a serious disadvantage in that greater or lesser amounts of methanesulfonic acid are decomposed to form sulfuric acid and carbon dioxide, as a result of which relatively costly hydrogen peroxide is consumed.

BRIEF SUMMARY OF THE INVENTION

The object of the present invention in comparison with the above mentioned prior art thus comprises an improved process for preparing silver compounds, in particular silver sulfonates.

The above mentioned object is achieved by a process for preparing a silver compound of the general formula (I)

$$RSO_3Ag \qquad (I)$$

where
R is an unsubstituted or substituted, linear or branched, saturated, monounsaturated or polyunsaturated alkyl or alkenyl radical having 1 to 9 carbon atoms or an unsubstituted or substituted aryl radical having 6 to 12 carbon atoms,
which comprises subjecting acid of the general formula (II)

$$RSO_3H \qquad (II)$$

where
R has the above mentioned meaning, to an electrolytic dissolution of the anode in a membraneless electrolysis cell having metallic silver as anode. In one preferred embodiment of the present invention, the acid of general formula II is halogen-substituted.

DETAILED DESCRIPTION OF THE INVENTION

Using the present invention it is possible to prepare silver compounds of the general formula (I) electrochemically, the preparation costs being more favorable than with the chemical processes described in the prior art. The technical implementation of membrane electrolysis cells is highly complex; the membranes used are generally very costly. Short service lives frequently additionally shorten the process.

The solutions of the silver compounds of the general formula (I) which are obtainable using the present invention can be used directly as electrolyte for electrodeposition and therefore do not necessarily require work-up to give the solid compounds. The solutions of these silver compounds are also stable over a long period.

If substituted alkyl-, alkenyl- or arylsulfonic acids are used in the context of the present invention, halogen-, hydroxy-, amino-, sulfo- or carboxyl-substituted derivatives are preferably to be emphasized here. In the context of the present invention, in particular, hydroxysulfonic acid or sulfosuccinic acid are thus included therein. Since the use of silver methanesulfonic acid and/or silver toluenesulfonic acid as electrolyte for chemical silvering is already known in the prior art, the process according to the invention is preferably used to prepare these compounds or their solutions. Therefore, it is necessary to use as acid of the general formula (II) methanesulfonic acid or toluenesulfonic acid directly. The present invention also contemplates mixtures of methanesulfonic acid and toluenesulfonic acid.

Particularly preferably in the context of the present invention, aqueous solutions of the abovementioned acids of the general formula (II) are used, in particular at a concentration of 5 to 70% by weight, or, for example, at a concentration of 30% strength sulfonic acid. When the electrolytic decomposition of metallic silver is carried out, therefore, the electrolyte can be taken off from time to time in the anodic region and supplemented with fresh aqueous sulfonic acid, for example methanesulfonic acid.

In the selection of the materials which are used for the metallic silver anode, the cost of the material plays an important role. Therefore, in the context of the present invention, it is particularly preferred to use metallic silver in the form of powder, granules, needles, shot, wire, rods, wool, foils or sheet. Those which may be particularly emphasized at this point are the inexpensive granules, which have a particular cost advantage in comparison with powder.

The membraneless electrolysis cell can be manufactured in accordance with conventional instructions and operated according to known processes. Therefore, in the context of the present invention, it is particularly preferred to carry out the reaction continuously at a temperature in the range from 15° C. to 80° C. at a voltage of 2 V to 20 V and anodic current density of 0.5 A/dm$^2$ to 15 A/dm$^2$.

To avoid simultaneous cathodic deposition of the silver, the anode region and cathode region must be separated from one another by structural means. By these arrangements, the migration of the silver ions in the electric field is greatly inhibited.

The silver compounds of the general formula (I) which are obtainable using the present invention are customarily used in the elecroplating industry in the form of aqueous solutions. Therefore, it is not necessary to prepare the compounds in crystalline, that is to say in solid, form. It is expedient, rather, to take off the aqueous solutions occurring in the course of the electrolytic process directly from the electrolysis bath when the desired concentration is reached, in order then to replace the electrolysis bath with fresh acid of the general formula (II), if appropriate in aqueous solution.

EXEMPLARY EMBODIMENTS

A 500 ml beaker served as membraneless electrolysis cell. As anode, use was made of conventional silver granules. The granule bed was connected as anode via a platinum wire. A platinum electrode served as cathode (suitable materials are also other inert metals or silver, which, although this is attacked slowly, does not contaminate the solution.

The anode surface was about 0.25 dm$^2$. The cathode surface was about 1 cm$^2$. An aqueous solution comprising about 30% methanesulfonic acid in demineralized water was used as electrolyte. At this concentration of acid, electrochemical dissolution of silver was greatest.

At a current of about 1 A and a voltage of about 7 V, the silver was then anodically dissolved. The uncooled electrolyte heated in this case to up to 51° C. To avoid simultaneous cathodic deposition of the silver, anode region and cathode region were separated from one another. Here, anode and cathode were spatially separated from one another structurally.

From time to time, the silver-enriched electrolyte in the anode region was then taken off and supplemented with the 30% strength methanesulfonic acid.

The silver methanesulfonate solutions taken off contained up to 405 g/l of Ag and about 5 to 10 g/l of $CH_3SO_3H$. A content of about 350 g/l of Ag and less than 50 g/l of $CH_3SO_3H$ could be achieved reproducibly.

The mean current efficiency was about 70%.

The solutions are water-white and stable for several months.

What is claimed is:

1. A process for preparing a silver compound of the general formula (I)

$$RSO_3Ag \qquad (I)$$

where R is an unsubstituted or substituted, linear or branched, saturated, monounsaturated or polyunsaturated alkyl or alkenyl radical having 1 to 9 carbon atoms or an unsubstituted or substituted aryl radical having 6 to 12 carbon atoms, which consists essentially of subjecting an acid of the general formula (II)

$$RSO_3H \qquad (II)$$

where R has the abovementioned meaning, to an electrolytic dissolution of an anode in a membraneless electrolysis cell having metallic silver as said anode.

2. The process as claimed in claim 1, wherein the acid of the general formula (II) is halogen-substituted.

3. The process as claimed in claim 1, wherein the acid of the general formula (II) is selected from the group consisting of methanesulfonic acid, toluenesulfonic acid, and mixtures thereof.

4. The process as claimed in claim 1 wherein an aqueous solution of the acid of the general formula (II) is used.

5. The process as claimed in claim 4 wherein the acid is present in said aqueous solution at a concentration of 5 to 70% by weight.

6. The process as claimed in claim 1 wherein the anode comprises metallic silver in the form of powder, granules, needles, shot, wire, rods, wool, foils or sheets.

7. The process as claimed in claim 1 wherein the reaction is carried out continuously at a temperature in the range from 15° C. to 80° C. at a voltage of 2 V to 20 V and anodic current density of 0.5 A/dm$^2$ to 15 A/dm$^2$.

8. The process as claimed in claim 1 wherein solution containing said compound of formula (I) is taken off from the electrolysis cell and continuously or batchwise replaced with fresh acid of the general formula (II).

* * * * *